US010080899B2

(12) United States Patent
Rezai et al.

(10) Patent No.: US 10,080,899 B2
(45) Date of Patent: Sep. 25, 2018

(54) SYSTEMS AND METHODS FOR TREATING AUTONOMIC INSTABILITY AND MEDICAL CONDITIONS ASSOCIATED THEREWITH

(71) Applicant: Ohio State Innovation Foundation, Columbus, OH (US)

(72) Inventors: Ali R. Rezai, Columbus, OH (US); Punit Agrawat, Worthington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/407,630

(22) Filed: Jan. 17, 2017

(65) Prior Publication Data

US 2017/0120055 A1    May 4, 2017

Related U.S. Application Data

(63) Continuation of application No. 14/848,966, filed on Sep. 9, 2015, now Pat. No. 9,561,370, which is a (Continued)

(51) Int. Cl.
*A61N 1/00* (2006.01)
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/3606* (2013.01); *A61N 1/36171* (2013.01)

(58) Field of Classification Search
CPC .............. A61N 1/0551; A61N 1/3606; A61N 1/36139; A61N 1/36171
See application file for complete search history.

(56) References Cited

U.S. PATENT DOCUMENTS 7,676,269 B2 * 3/2010 Yun ..................... A61K 31/137
                                                                607/2
8,452,387 B2   5/2013 Osorio et al.
(Continued)

FOREIGN PATENT DOCUMENTS

WO   2004110551 A2   12/2004
WO   2006007048 A2   1/2006
WO   2006055849 A1   5/2006

OTHER PUBLICATIONS

International Search Report corresponding to Appl. No. PCT/US2014/022386, dated Jun. 23, 2014, 4 pages.

*Primary Examiner* — George Manuel
(74) *Attorney, Agent, or Firm* — Meunier Carlin & Curfman LLC (57) ABSTRACT

One aspect of the present disclosure relates to a closed-loop therapy system for treating autonomic instability or a medical condition associated therewith in a subject. The therapy delivery system can include a sensing component, a delivery component, and a controller. The sensing component can be configured to detect at least one physiological parameter associated with autonomic instability or a medical condition associated therewith. The delivery component can be configured for implantation on or about an autonomic nervous tissue target or a spinal nervous tissue target. The controller can be configured to automatically coordinate operation of the sensing and delivery components. The controller can also be configured to deliver an electrical signal to the delivery component to modulate activity at the autonomic nervous tissue target or a spinal nervous tissue target and effectively treat autonomic instability or a medical condition associated therewith.

16 Claims, 8 Drawing Sheets

Related U.S. Application Data continuation-in-part of application No. PCT/US2014/022386, filed on Mar. 10, 2014.

(60) Provisional application No. 61/776,099, filed on Mar. 11, 2013.

(56) References Cited

U.S. PATENT DOCUMENTS

| | | |
|---|---|---|
| 2006/0085046 A1 | 4/2006 | Rezai et al. |
| 2006/0135998 A1 | 6/2006 | Libbus et al. |
| 2007/0142871 A1 | 6/2007 | Libbus et al. |
| 2008/0015659 A1 | 1/2008 | Zhang et al. |
| 2010/0274321 A1 | 10/2010 | Libbus |
| 2013/0190838 A1 | 7/2013 | Caparso |

* cited by examiner

SYSTEMS AND METHODS FOR TREATING AUTONOMIC INSTABILITY AND MEDICAL CONDITIONS ASSOCIATED THEREWITH

RELATED APPLICATION

This application is a continuation application of U.S. application Ser. No. 14/848,966, filed on Sep. 9, 2015, which is a continuation-in-part application of PCT Application No. PCT/US2014/022386, filed on Mar. 10, 2014, which claims priority to U.S. Provisional Patent Application Ser. No. 61/776,099, filed Mar. 11, 2013, the entirety of all applications is hereby incorporated by reference for all purposes.

TECHNICAL FIELD

The present disclosure relates generally to neuromodulatory devices, systems and methods, and more particularly to devices, systems, and methods for treating autonomic instability and medical conditions associated therewith.

BACKGROUND

Dysfunction of the autonomic nervous system (ANS) is known as dysautonomia. The ANS regulates unconscious body functions, including heart rate, blood pressure, temperature regulation, gastrointestinal secretion, and metabolic and endocrine responses to stress, such as the "fight or flight" syndrome. As regulating these functions involves various and multiple organ systems, dysfunctions of the ANS encompass various and multiple disorders. Autonomic dysfunction or instability is a common condition that influences many areas of medicine, such as neurological disorders.

SUMMARY

The present disclosure relates generally to neuromodulatory devices, systems and methods, and more particularly to devices, systems, and methods for treating autonomic instability or a medical condition associated therewith.

One aspect of the present disclosure relates to a closed-loop therapy system for treating autonomic instability or a medical condition associated therewith in a subject. The therapy delivery system can include a sensing component, a delivery component, and a controller. The sensing component can be configured to detect at least one physiological parameter associated with autonomic instability or a medical condition associated therewith. The delivery component can be configured for implantation on or about an autonomic nervous tissue target or a spinal nervous tissue target. The controller can also be coordinate operation of the sensing and delivery components. The controller can also be configured to deliver an electrical signal to the delivery component to modulate activity at the autonomic nervous tissue target or a spinal nervous tissue target and effectively treat autonomic instability or the medical condition associated therewith.

Another aspect of the present disclosure relates to a closed-loop therapy delivery system for treating autonomic instability a medical condition associated therewith in a subject. The therapy delivery system can consist of a sensing component, a delivery component, and a co roller. The sensing component can be configured to detect at least one physiological parameter associated with autonomic instability or the medical condition associated therewith. The delivery component can be configured for implantation on or about a cervicothoracic ganglion. The controller can be configured to automatically coordinate operation of the sensing and delivery components. The controller can be configured to deliver an electrical signal to the delivery component to modulate activity of the cervicothoracic ganglion and effectively treat the autonomic instability or the medical condition associated therewith.

Another aspect of the present disclosure relates to a method for treating autonomic instability or a medical condition associated therewith in a subject. One step of the method can include placing a therapy delivery device into electrical communication with an autonomic nervous tissue target or a spinal nervous tissue target associated with autonomic instability or a medical condition associated therewith. Next, the therapy delivery device can be activated to deliver an electrical signal to the autonomic nervous tissue target or a spinal nervous tissue target effectively treat autonomic instability or the medical condition associated therewith in the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Unless defined otherwise, all technical and scientific terms used herein have the same meaning as is commonly understood by one of skill in the art to which the present disclosure pertains.

In the context of the present disclosure, the term "autonomic nervous tissue" can refer to any tissues of the sympathetic nervous system (SNS) or the parasympathetic nervous system (PNS) including, but not limited to, neurons, axons, fibers, tracts, nerves, plexus, afferent plexus fibers, efferent plexus fibers, ganglia, pre-ganglionic fibers, post-ganglionic fibers, afferents, efferents, and combinations thereof.

As used herein, the terms "epidural space" or "spinal epidural space" can refer to an area in the interval between the dural sheath and the wall of the spinal canal. In some instances, at least a portion of a therapy delivery device or a therapy delivery system may be implanted in the epidural space.

As used herein, the term "subdural" can refer to the space between the dura mater and arachnoid membrane. In some instances, at least a portion of a therapy delivery device or a therapy delivery system may be implanted in the subdural space.

As used herein, the phrase "spinal nervous tissue" can refer to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord.

As used herein, the term "subject" can be used interchangeably with the term "patient" and refer to any warm-blooded organism including, but not limited to, human beings, pigs, rats, mice, dogs, goats, sheep, horses, monkeys, apes, farm animals, livestock, rabbits, cattle, etc.

As used herein, the terms "modulate" or "modulating" with reference to an automatic nervous tissue target or spinal nervous tissue target can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, ultrasound, optical, chemical, or a combination of two or more of these. The terms "modulate" or "modulating" can also be used to refer to a masking, altering, overriding, or restoring of neuronal activity.

As used herein, the terms "substantially blocked" or "substantially block" when used with reference o nervous tissue activity can refer to a complete (e.g., 100%) or partial inhibition (e.g., less than 100%, such as about 90%, about 80%, about 70%, about 60%, or less than about 50%) of nerve conduction through the nervous tissue.

As used herein, the term "activity" when used with reference to autonomic or spinal nervous tissue can, in some instances, refer to the ability of a nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on autonomic or spinal nervous tissue.

As used herein, the terms "autonomic instability" or "autonomic dysfunction can refer to any abnormal fluctuation in sympathetic and/or parasympathetic tone above or below a normal or baseline (e.g., healthy) level. Such abnormal fluctuation can be chronic (e.g., months, years, etc.) or acute (e.g., hours, days, etc.).

As used herein, the terms "medical condition associated with autonomic instability" or "medical condition associated with autonomic dysfunction" can refer to any disease, disorder, sign, or symptom that is associated with, or results at least in park from, autonomic instability or dysfunction. In some instances, a medical condition associated with autonomic instability or dysfunction can include neurodegenerative disease, such as Parkinson's disease, multiple systems atrophy, other atypical parkinsonian syndromes, neuropathy, inflammatory/autoimmune disease, demyelinating disorders, such as Guillian Barre Syndrome, paraneoplastic syndromes, infectious etiologies e.g., botulism). Chagas, addictions (e.g., alcoholism), mitochondrial disorders, spinal cord injury, brain injury, concussions, other trauma, complex regional pain syndrome, heavy metal toxicity, other toxicities, amyloidosis, porphyria, and also inherited disorders such as Fabry's disease and Hereditary Sensory Autonomic Neuropathy syndromes. In other instances, a medical condition associated with autonomic instability or dysfunction can be characterized by one or more signs or symptoms, such as problems with blood pressure regulation (e.g., orthostatic hypotension and hypertension), cardiac arrhythmia (e.g., tachycardia/bradycardia), dysfunctional gastrointestinal motility (e.g., reflux, gastroparesis), genitourinary trouble (e.g., urinary incontinence, overactive bladder, erectile dysfunction), impaired sweat response (e.g., hyperhidrosis or anhidrosis), dysfunctional temperature regulation, and also changes in salivary production (e.g., sialorrhea), trouble with ambulation due to lightheadedness/near syncope, recurrent syncope, severe reflux, trouble with swallowing, difficulty clearing oral secretion, reoccurring aspiration, poor gastrointestinal absorption, reoccurring bowel obstructions, unexplained fevers, constant sweating, hot/cold intolerance, frequent urination, urinary incontinence, and recurrent urinary tract infections.

As used herein, the terms "treat" or "treating" can refer to therapeutically regulating, preventing, improving, alleviating the symptoms of, and/or reducing the effects of autonomic instability or a medical condition associated therewith. As such, treatment also includes situations ere autonomic instability or a medical condition associated therewith, or at least symptoms associated therewith, is completely inhibited, e.g., prevented from happening or stopped (e.g., terminated) such that the subject no longer suffers from autonomic instability or the medical condition associated therewith, or at least the symptoms that characterize autonomic instability or the medical condition associated therewith. in some instances, the terms can refer to improving or normalizing at least one function of an organ or organ tissue affected by an imbalanced sympathetic and/or parasympathetic input.

As used herein, the term "in communication" can refer to at least a portion of a therapy delivery device or therapy delivery system being adjacent, in the general vicinity, in close proximity, or directly next to and/or directly on an autonomic nervous tissue target or spinal nerve target associated with autonomic instability or a medical condition associated therewith. In some instances, the term can mean that at least a portion of a therapy delivery device or therapy delivery system "in communication" with an autonomic nervous tissue target or a spinal nervous tissue target if application of a therapy signal (e.g., an electrical and/or chemical signal) thereto results in a modulation of neuronal activity to elicit a desired response, such as modulation of a sign or symptom associated with autonomic instability or a medical condition associated therewith.

As used herein, the singular forms "a," "an" and "the" can include the plural forms as well, unless the context clearly indicates otherwise. ft will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also he appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

A brief discussion of the pertinent neurophysiology is provided to assist the reader with understanding certain aspects of the present disclosure.

The Autonomic Nervous Sys (ANS)

The nervous system is divided into the somatic nervous system and the ANS. In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism. The ANS acts through a balance of its two components: the sympathetic nervous system (SNS) and the parasympathetic nervous system (PNS), which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

Figure 1:
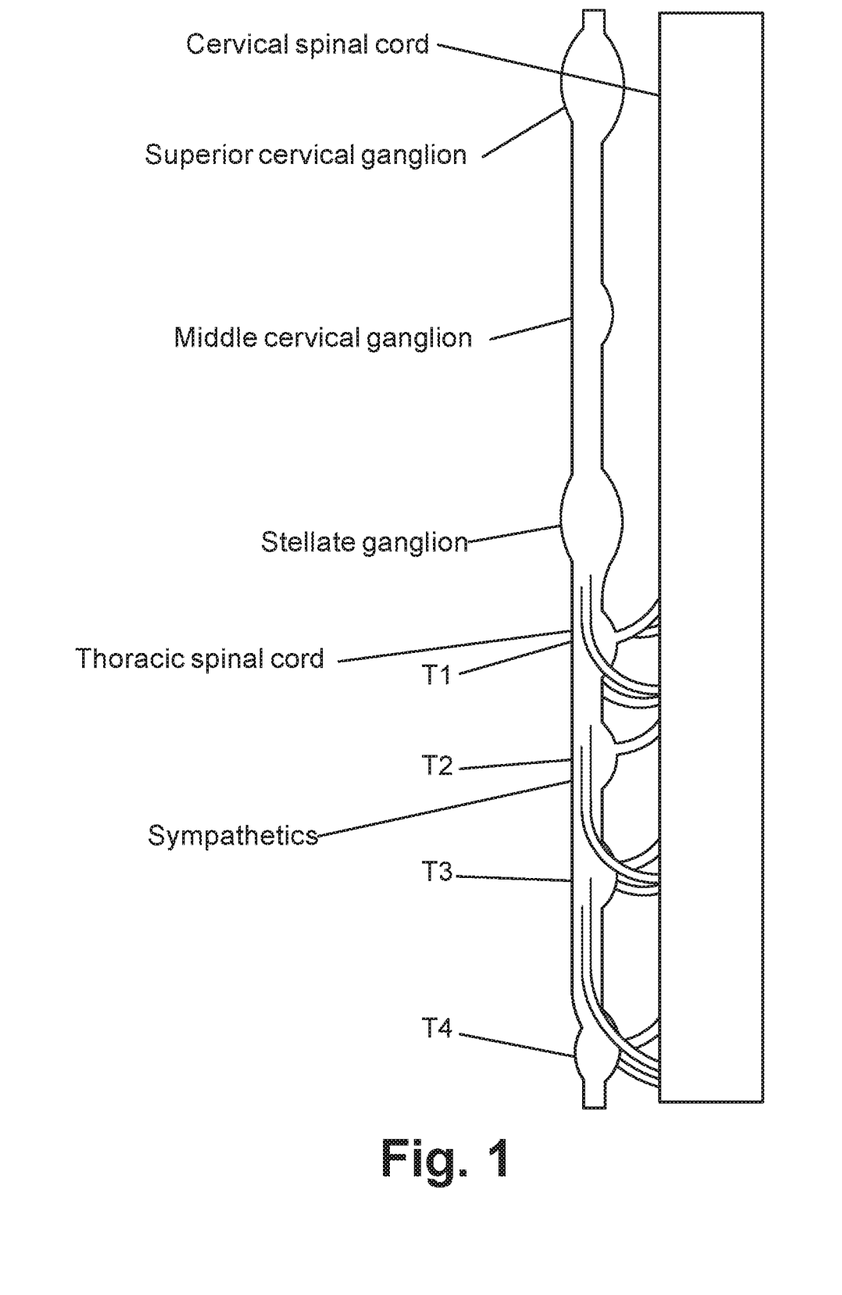
FIG. 1 is schematic illustration showing the cervical and upper thoracic portions of the sympathetic nerve chain and the spinal cord.

The SNS is the part of the ANS comprising nerve fibers that leave he spinal cord in the thoracic and lumbar regions and supply viscera and blood vessels by way of a chain of sympathetic ganglia (also referred to as the sympathetic chain, sympathetic trunk or the gangliated cord) running on each side of the spinal column, which communicate with the central nervous system via a branch to a corresponding spinal nerve. The sympathetic trunks extend from the base of the skull to the coccyx. The cephalic end of each is continued upward through the carotid canal into the skull, and forms a plexus on the internal carotid artery; the caudal ends of the trunks converge and end in a single ganglion, the ganglion impar, placed in front of the coccyx. As partly shown in FIG. 1, the ganglia of each trunk are distinguished as cervical, thoracic, lumbar, and sacral and, except in the neck, they closely correspond in number to the vertebrae.

The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine. The action of noradrenaline on a particular structure, such as a gland or muscle, is excitatory in some cases and inhibitory in others. At excitatory terminals, ATP may be released along with noradrenaline. Activation of the S NS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

The PNS is the part of the ANS controlling a variety of autonomic functions including, but not limited to, involuntary muscular movement of blood vessels and gut and glandular secretions from eye, salivary glands, bladder, rectum and genital organs. The vagus nerve is part of the PNS. Parasympathetic nerve fibers are contained within the last five cranial nerves and the last three spinal nerves and terminate at parasympathetic ganglia near or in the organ they supply. The actions of the PNS are broadly antagonistic to those of the SNS—lowering blood pressure, slowing heartbeat, stimulating the process of digestion etc. The chief neurotransmitter in the PNS is acetylcholine. Neurons of the parasympathetic nervous system emerge from the brainstem as par of the Cranial nerves III, VII, IX and X (vagus nerve) and also from the sacral region of the spinal cord via Sacral nerves. Because of these origins, the PNS is often referred to as the "craniosacral outflow".

In the PNS, both pre- and post-ganglionic neurons are cholinergic (i.e., they utilize the neurotransmitter acetylcholine). Unlike adrenaline and noradrenaline, which the body takes around 90 minutes to metabolize, acetylcholine is rapidly broken down after release by the enzyme cholinesterase. As a result the effects are relatively brief in comparison to the SNS.

Each pre-ganglionic parasympathetic neuron synapses with just a few post-ganglionic neurons, which are located near, or in, the effector organ, a muscle or gland. As noted above, the primary neurotransmitter in the PNS is acetylcholine such that acetylcholine is the neurotransmitter at all the pre- and many of the post-ganglionic neurons of the PNS. Some of the post-ganglionic neurons, however, release nitric oxide as their neurotransmitter.

The Central Nervous System (CNS)

The spinal cord (FIG. 2) is part of the CNS, which extends caudally and is protected by the bony structures of the vertebral column. It is covered by the three membranes of the CNS, i.e., the dura mater, arachnoid and the innermost pia mater. In most adult mammals, it occupies only the upper two-thirds of the vertebral canal as the growth of the bones composing the vertebral column is proportionally more rapid than that of the spinal cord. According to its rostrocaudal location, the spinal cord can be divided into four parts: cervical: thoracic; lumbar; and sacral. Two of these are marked by an upper (cervical) and a lower (lumbar) enlargement.

Alongside the median sagittal plane, the anterior and the posterior median fissures divide the cord into two symmetrical portions, which are connected by the transverse anterior and posterior commissures. On either side of the cord the anterior lateral and posterior lateral fissures represent the points where the ventral and dorsal rootlets (later roots) emerge from the cord to form the spinal nerves. Unlike the brain, in the spinal cord the grey matter is surrounded by the white matter at its circumference. The white matter conventionally divided into the dorsal, dorsolateral, lateral, ventral and ventrolateral funiculi.

Each half of the spinal grey matter is crescent-shaped, although the arrangement of the grey matter and its proportion to the white matter varies at different rostrocaudal levels. The grey matter can be divided into the dorsal horn, intermediate grey, ventral horn, and a centromedial region surrounding the central canal (central grey matter). The white matter gradually ceases towards the end of the spinal cord and the grey matter blends into a single mass (conus terminalis) where parallel spinal roots form the so-called cauda equine.

The present disclosure relates generally to neuromodulatory devices, systems and methods, and more particularly to devices, systems, and methods for treating autonomic instability or a medical condition associated therewith. The ANS regulates the intrinsic function and balance of each body organ and maintains homeostasis and balance of the cardiovascular, hormonal, and sleep systems. Neuromodulation of the ANS is a precise, controlled, and highly targeted approach to influence and impact the function and dysfunction in humans. Neuromodulation according to the present disclosure can improve the function, activate, inhibit, modulate, and impact the intrinsic autonomic and circadian neural tone, as well as normalize or regulate the function and sympathetic/parasympathetic output to the various body systems (e.g., cardiovascular, gastrointestinal, and body homeostasis), which are impacted in autonomic instability and dysfunction. As described in detail below, the present disclosure advantageously provides, in some instances, devices, systems, and methods for uncoupling dysfunctional nerve signals from the brain to the ANS (as well as ascending signals into the CNS), as well as dysfunctional nerve signals from the ANS to peripheral tissues (e.g., cardiac, gastric, vascular, immunological, and other related tissues/organs) to effectively normalize or regulate the ANS (e.g., the SNS). By employing such devices, systems and methods, the present disclosure can treat autonomic instability and medical conditions associated therewith.

Therapy Delivery Devices and Systems

In one aspect, the present disclosure includes various therapy delivery devices (not shown) and related systems configured to treat autonomic instability and medical conditions associated therewith in a subject. In some instances, therapy delivery devices that may be used to practice the present disclosure may be positioned directly on or in an autonomic nervous tissue target or spinal nervous tissue target. In other instances, therapy delivery devices that may be used to practice the present disclosure can be positioned below the skin of a subject, but not directly on or in an autonomic nervous tissue target or spinal nervous tissue target. In further instances, therapy delivery devices that may be used to practice the present disclosure can comprise external devices, e.g., positioned in a lumen adjacent an autonomic nervous tissue target or spinal nervous tissue target. In still further instances, therapy delivery devices used to practice the present disclosure can comprise an external device, e.g., positioned on the skin of a subject adjacent an autonomic nervous tissue target or spinal nervous tissue target. Therapy delivery devices can be temporarily or permanently implanted within, on, or otherwise associated with a subject suffering from, afflicted by, or suspected of having autonomic instability or a medical condition associated therewith.

Therapy delivery devices of the present disclosure can be configured to deliver various types of therapy signals to an autonomic nervous tissue target or spinal nervous tissue target. For example, therapy delivery devices of the present disclosure can be configured to deliver only electrical energy, only magnetic energy, only a pharmacological or biological agent, or a combination thereof. In one example, therapy delivery devices of the present disclosure can comprise at least one electrode and an integral or remote power source, which is in electrical communication with the one or more electrodes and configured to produce one or more electrical signals (or pulses). In another example, therapy delivery devices can include a pharmacological or biological agent reservoir, a pump, and a fluid dispensing mechanism. Non-limiting examples of pharmacological and biological agents can include chemical compounds, drugs (e.g., prazosin, clonidine), nucleic acids, polypeptides, stem cells, toxins (e.g., botulinum), as well as various energy forms, such as ultrasound, radiofrequency (continuous or pulsed), magnetic waves, cryotherapy, and the like. In yet another example, therapy delivery devices can be configured to deliver magnetic nerve stimulation with desired field focality and depth of penetration. One skilled in the art will appreciate that combinations of the therapy delivery devices above configurations are also included within scope of the present disclosure.

Figure 2:
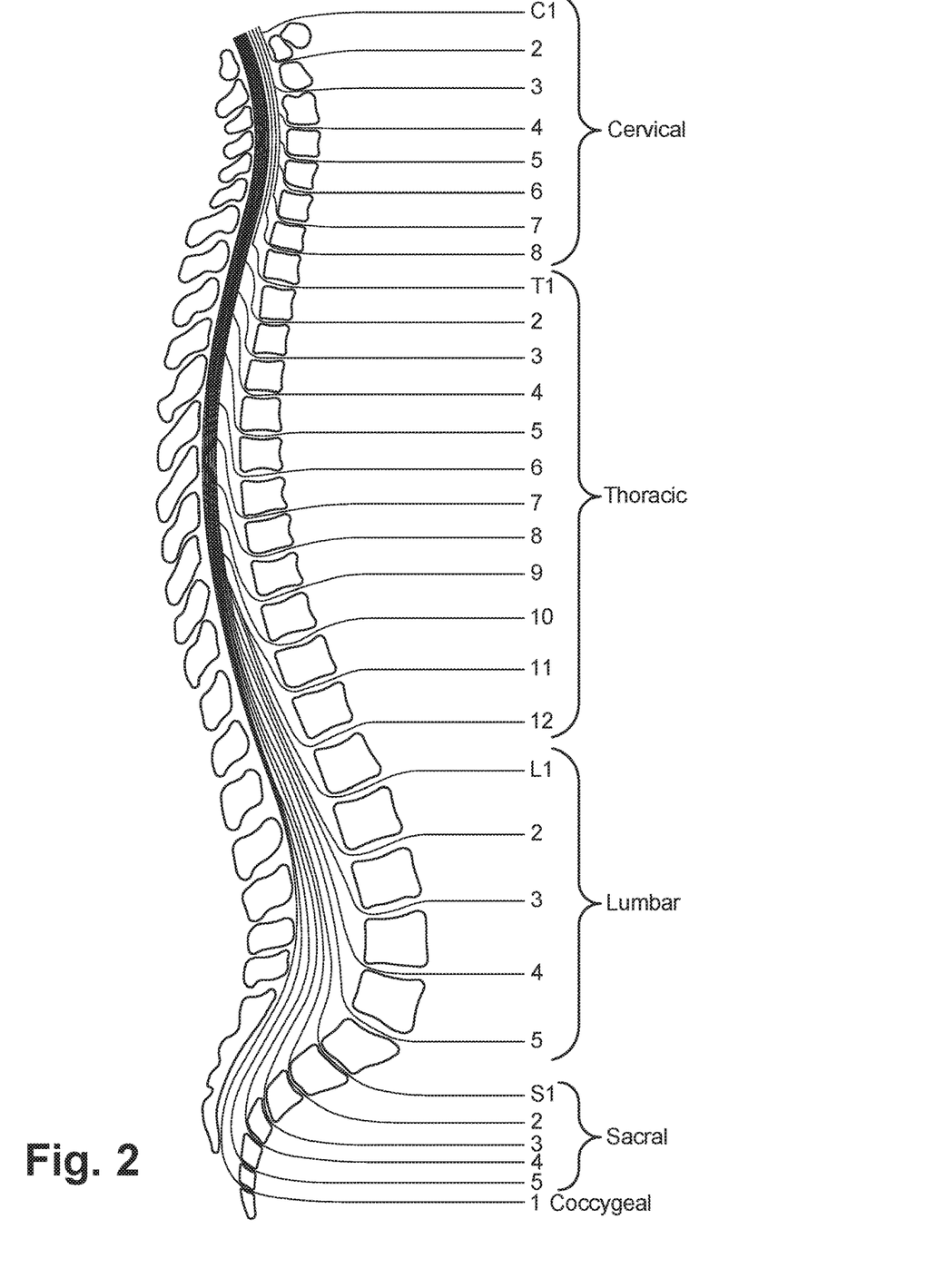
FIG. 2 is a schematic illustration of a human spinal cord and associated vertebrae.
Figure 3:
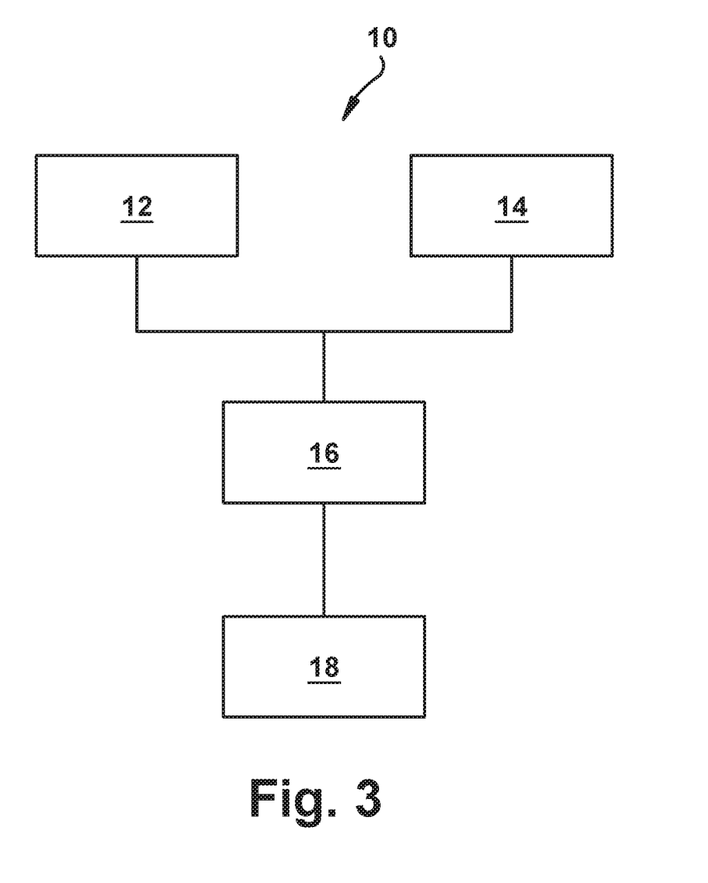
FIG. 3 is a schematic illustration showing a closed-loop therapy delivery system for treating autonomic instability or a medical condition associated therewith configured according to one aspect of the present disclosure.

In some instances, therapy delivery devices can comprise a stimulator (or inhibitor), such as an electrode, a controller or programmer, and one or more connectors (e.g., leads) for connecting the stimulating (or inhibiting) device to the controller. In one example, which is described in further detail below, the present disclosure can include a closed-loop therapy delivery system 10 (FIG. 2) for treating autonomic instability or a medical condition associated therewith. As shown in FIG. 2, the therapy delivery system 10 can include a sensing component 12, a delivery component 14, a controller 16, and a power source 18. Each of the sensing component 12, delivery component 14, controller 16, and power source 18 can be in electrical communication with one another (e.g., via a physical connection, such as a lead, or a wireless link). In some instances, each of the sensing and delivery components 12 and 14 can comprise an electrode. In other instances, the delivery component 14 can comprise a coil configured to deliver magnetic stimulation. In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode can be controllable to provide output signals that may be varied in voltage, frequency, pulse-width, current and intensity. The electrode can also provide both positive and negative current flow from the electrode and/or is capable of stopping current flow from the electrode and/or changing the direction of current flow from the electrode. In some instances, therapy delivery devices can include an electrode that is controllable, i.e., in regards to producing positive and negative current flow from the electrode, stopping current flow from the electrode, changing direction of current flow from the electrode, and the like. In other instances, the electrode has the capacity for variable output, linear output and short pulse-width, as well as paired pulses and various waveforms (e.g., sine wave, square wave, and the like).

The power source 18 can comprise a battery or generator, such as a pulse generator that is operatively connected to an electrode via the controller 16. The power source 18 can be configured to generate an electrical signal or signals. In one example, the power source 18 can include a battery that is rechargeable by inductive coupling. The power source 18 may be positioned in any suitable location, such as adjacent the electrode (e.g., implanted adjacent the electrode), or a remote site in or on the subject's body or away from the subject's body in a remote location. An electrode may be connected to the remotely positioned power source 18 using wires, e.g., which may be implanted at a site remote from the electrode(s) or positioned outside the subject's body. In one example, an implantable power source 18 analogous to a cardiac pacemaker may be used.

The controller 16 can be configured to control the pulse waveform, the signal pulse width, the signal pulse frequency, the signal pulse phase, the signal pulse polarity, the signal pulse amplitude, the signal pulse intensity, the signal pulse duration, and combinations thereof of an electrical signal. In other instances, the controller 16 can be configured to control delivery of magnetic energy or stimulation to the delivery component 14. The controller 16 may be used to convey a variety of currents and voltages to one or more electrodes and thereby modulate the activity of a target sympathetic nervous tissue. The controller 16 may be used to control numerous electrodes independently or in various combinations as needed to provide stimulation or inhibition of nerve activity. In some instances, an electrode may be employed that includes its own power source, e.g., which is capable of obtaining sufficient power for op-ration from surrounding tissues in the subject's body, or which may be powered by bringing a power source 18 external to the subject's body into contact with the subject's skin, or which may include an integral power source.

The electrical signal (or signals) delivered by the controller 16 to the delivery component 14 may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA, and even more specifically from about 0.1 to about 25 mA. Similarly, the voltage may range from about 0.1 millivolt to about 25 volts, or about 0.5 to about 4000 Hz, with a pulse-width of about 5 microseconds to about 5000 microseconds, and more specifically, from about 10 to about 1000 microseconds. The frequency may range from about 5 Hz to about 25,000 Hz. In one example, the electrical signal can be oscillatory. The type of stimulation may vary and involve different waveforms known to the skilled artisan. For example, the stimulation be based on the H waveform found in nerve signals (i.e., Hoffman Reflex). In another example, different forms of interferential stimulation may be used.

To increase nerve activity in a portion of the ANS, for example, voltage or intensity may range from about 1 millivolt to about 1 volt or more, e.g., 0.1 to about 50 mA or volts (e.g., from about 0.2 volts to about 20 volts), and the frequency may range from about 1 Hz to about 10,000 Hz, e.g., about 1 Hz to about 1000 Hz (e.g., from about 2 Hz to about 100 Hz). In some instances, pure DC and/or AC voltages may be employed. The pulse-width may range from about 1 microsecond to about 10,000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, stimulation may be applied for as long as about 1 minute or more, e.g., about several minutes or more (e.g., about 30 minutes or more).

To decrease activity in a portion of the ANS, for example, voltage or intensity may range from about 1 millivolt to about 1 volt or more, e.g., 0.1 to about 50 mA or volts (e.g., from about 0.2 s volt to about 20 volts), and the frequency may range from about 1 Hz to about 2500 Hz, e.g., about 50 Hz to about 2500 Hz. In one example, an electrical signal can have a frequency range of about 10,000 Hz or greater (e.g., high frequency stimulation) to effectively block nerve conduction, and more specifically from about 10,000 Hz to about 25,000 Hz. In some instances, pure DC and/or AC voltages may be employed. The pulse-width may range from about 1 microseconds to about 10,000 microseconds or more, e.g., from about 10 microseconds to about 2000 microseconds (e.g., from about 15 microseconds to about 1000 microseconds). The electrical signal ay be applied for at least about 1 millisecond or more, e.g., about 1 second (e.g., about several seconds). In some instances, the electrical energy may be applied for as long as about 1 minute or more, e.g., about several minutes or more (e.g., about 30 minutes or more may be used), The electrode may be mono-polar, bipolar or multi-polar. To minimize the risk of an immune response triggered by the subject against the therapy delivery device, and also to minimize damage thereto (e.g., corrosion from other biological fluids, etc.), the electrode (and any wires and optional housing materials) can be made of inert materials, such as silicon, metal, plastic and the like. In one example, a therapy delivery device can include a multi-polar electrode having about four exposed contacts (e.g., cylindrical contacts).

As discussed above, the controller 16 (or a programmer) may be associated with a therapy delivery device. The controller 16 can include, for example, one or more microprocessors under the control of a suitable software program. Other components of a controller 16, such as an analog-to-digital converter, etc., will be apparent to those of skill in the art. In some instances, the controller 16 can be configured to record and store data indicative of the intrinsic autonomic tone or activity in the subject. Therefore, the controller 16 can be configured to apply one or more electrical signals to the delivery component 14 when the intrinsic autonomic tone or activity of a subject increases or decreases above a certain threshold value (or range of values), such as a normal or baseline level.

Therapy delivery devices can be pre-programmed with desired stimulation parameters. Stimulation parameters can be controllable so that an electrical signal may be remotely modulated to desired settings without removal of the electrode from its target position. Remote control may be performed, e.g., using conventional telemetry with an implanted power source 18, an implanted radiofrequency receiver coupled to an external transmitter, and the like. In some instances, some or all parameters of the electrode may be controllable by the subject, e.g., without supervision by a physician. In other instances, some or all parameters of the electrode may be automatically controllable by a controller 16.

In one example, the therapy delivery device can be configured for percutaneous placement or implantation. In this instance, the therapy delivery device can comprise one or more implantable electrodes shaped or configured, for example, as a wire, a rod, a filament, a ribbon, a cord, a tube, a formed wire, a flat strip, or a combination thereof. In one example, one or more of the electrodes can comprise a laminotomy electrode array. Laminotomy electrodes, for example, generally have a flat paddle configuration and typically possess a plurality of electrodes (e.g., 2, 3, 4 or more) arranged on the paddle. The arrangement of electrodes on the paddle may be in rows and columns, staggered, spaced, circular, or any other arrangement that will position the electrodes for optimal delivery of electrical energy. The one or more implantable electrodes may, be controlled individually, in series, in parallel, or any other manner desired. Once implanted, the implantable electrode(s) may be held in position using any method known to the skilled artisan, much as stitches, epoxy, tape, glue, sutures, or a combination thereof.

In another example, the therapy delivery device can be configured for intravascular or intraluminal placement or implantation. In some instances, a therapy delivery device configured for intravascular or intraluminal placement or implantation can be configured in an identical or similar manner as the expandable electrode disclosed in U.S. patent application Ser. No. 11/641,331 to Greenberg et al, (hereinafter, "the '331 application"). In one example, the therapy delivery device cat be configured for intravascular or intraluminal placement or implantation at an implantation site that is adjacent, or directly adjacent, an autonomic nervous tissue target or spinal nervous tissue target.

In yet another example, the therapy delivery device can be configured for transcutaneous neuromodulation. In some instances, transcutaneous neuromodulation can include positioning a delivery component (e.g., an electrode or magnetic coil) on a skin surface so that a therapy signal (e.g., an electrical signal or magnetic field) can be delivered to an autonomic nervous tissue target or spinal nervous tissue target. Transcutaneous neuromodulation can additionally include partially transcutaneous methods (e.g., using a fine, needle-like electrode to pierce the epidermis). In other instances, a surface electrode (or electrodes) or magnetic coil can be placed into electrical contact with an autonomic nervous tissue target or spinal nervous tissue target associated with autonomic instability or a medical condition associated therewith. Non-limiting examples of transcutaneous neuromodulation devices that may be used for treating autonomic instability or a medical condition associated therewith are discussed below.

In one example, an electrical signal used for transcutaneous neuromodulation may be constant, varying and/or modulated with respect to the current, voltage, pulse-width, cycle, frequency, amplitude, and so forth (e.g., the current may be between about 1 to 100microampere), about 10 V (average), about 1 to about 1000 Hz or more, with a pulse-width of about 250 to about 500 microseconds, In another example, the present disclosure can include a therapy delivery device or system configured for transcutaneous neuromodulation using magnetic stimulation. A magnetic stimulation device or system can generally include a pulse generator (e.g., a high current pulse generator) and a stimulating coil capable of producing magnetic pulses with desired field strengths. Other components of a magnetic stimulation device can include transformers, capacitors, microprocessors, safety interlocks, electronic switches, and the like. In operation, the discharge current flowing through the stimulating coil can generate the desired magnetic field or lines of force. As the lines of force cut through tissue (e.g., neural tissue), a current is generated in that tissue. If the induced current is of sufficient amplitude and duration such that the cell membrane is depolarized, nervous tissue will be stimulated in the same manner as conventional electrical stimulation. It is therefore worth noting that a magnetic field is simply the means by which an electrical current is generated within the nervous tissue, and that it is the electrical current, and not the magnetic field, which causes the depolarization of the cell membrane and thus stimulation of the target nervous tissue. Thus, in some instances, advantages of magnetic over electrical stimulation can include: reduced or sometimes no pain; access to nervous tissue covered by poorly conductive structures; and stimulation of nervous tissues lying deeper in the body without requiring invasive techniques or very high energy pulses.

Therapy delivery devices can be part of an open- or closed-loop system. In an open-loop system, for example, a physician or subject may, at any time, manually or by the use of pumps, motorized elements, etc., adjust treatment parameters, such as pulse amplitude, pulse-width, pulse frequency, duty cycle, dosage amount, type of pharmacological or biological agent, etc. Alternatively, in a closed-loop system 10 (as discussed above), treatment parameters (e.g., electrical signals) may be automatically adjusted in response to a sensed physiological parameter or a related symptom or sign indicative of the extent and/or presence of autonomic instability or a medical condition associated therewith. In a closed-loop feedback system 10, a sensing component 12 can comprise a sensor (not shown in detail) that senses a physiological parameter associated with autonomic instability or a medical condition associated therewith can be utilized. More detailed descriptions of sensors that may be employed in closed-loop systems, as well as other examples of sensors and feedback control techniques that may be employed as part of the present disclosure are disclosed in U.S. Pat. No. 5,716,377. One or more sensing components 12 can be implanted on or in any tissue or organ of a subject. For example, a sensing component 12 can be implanted in or on a component of the ANS, such as nerves, ganglia, afferents or efferents, or the spinal cord. Alternatively or additionally, a sensing component 12 can be implanted on or in a body organ and/or an anatomical connection thereof.

It should be appreciated that implementing a therapy delivery device as part of a closed-loop system can include placing or implanting a therapy delivery device on or within a subject at an autonomic nervous tissue target or spinal nervous tissue target, sensing a physiological parameter associated with autonomic instability or a medical condition associated therewith, and then activating the therapy delivery device to apply an electrical signal to adjust application of the electrical signal, such as adjusting the stimulation parameters as described herein, to the autonomic nervous tissue target or spinal nervous tissue target in response to the sensor signal. In some instances, such physiological parameters can include any characteristic, sign, symptom, or function associated with autonomic instability or a medical condition associated therewith, such as a chemical moiety or nerve activity (e.g., electrical activity). Examples of such chemical moieties and nerve activities can include the activity of autonomic ganglia (or an autonomic ganglion), the activity of a spinal cord segment or spinal nervous tissue associated therewith, protein concentrations, electrochemical gradients, hormones (e.g., cortisol), neuroendocrine markers, such as corticosterone, norepinephrine and melatonin, electrolytes, laboratory values, vital signs (e.g., blood pressure), markers of locomotor activity, cardiac markers (e.g., EKG RR intervals), or other signs and biomarkers associated with autonomic instability or a medical condition associated therewith.

Methods

Another aspect of the present disclosure includes a method for treating autonomic instability or a medical condition associated therewith in a subject. In general, methods of the present disclosure can include the steps of: providing a therapy delivery device; placing the therapy delivery device into electrical communication with an autonomic nervous tissue target or spinal nervous tissue target associated with autonomic instability or a medical condition associated therewith; and activating the therapy delivery device to deliver a therapy signal (e.g., an electrical signal or magnetic field) to the autonomic nervous tissue target or spinal nervous tissue target to effectively treat autonomic instability or the medical condition associated therewith. Subjects treatable by the present disclosure can, in some instances, be diagnosed with (or suspected of having) autonomic instability or a medical condition associated therewith as well as one or more related or unrelated medical conditions. Non-limiting examples of medical conditions that can be co-treated by the methods of the present disclosure can include substance abuse, sleep deprivation or sleep disorders, psychiatric disturbances or diseases, impulse control disorders, cardiovascular disease, metabolic disorders (e.g., diabetes), and major depressive episodes.

In some instances, the step of placing a therapy delivery device into electrical communication with an autonomic nervous tissue target or spinal nervous tissue target can entail different surgical and/or medical techniques depending, for example, upon the target tissue. In some instances, a therapy delivery device can be surgically placed into electrical communication with an autonomic nervous tissue target or spinal nervous tissue target via a percutaneous or endoscopic route. In other instances, a therapy delivery device can be placed into electrical communication with an autonomic nervous tissue target or spinal nervous tissue target via an intravascular or intraluminal route. In further instances, a therapy delivery device can be placed into electrical communication with an autonomic nervous tissue target or spinal nervous tissue target via a transcutaneous approach.

Examples of autonomic nervous tissue targets into which a therapy delivery device may be placed into electrical communication with can include, but are not limited to, any tissues of the SNS or the PNS. In some instances, autonomic nervous tissue targets into which a therapy delivery device may be placed into electrical communication with can include a sympathetic chain ganglion, an efferent of a sympathetic chain ganglion, or an afferent of a sympathetic chain ganglion. In other instances, the sympathetic chain ganglion can be a cervical sympathetic ganglion, a thoracic sympathetic ganglion, or a stellate ganglion. Examples of cervical sympathetic ganglia can include an upper cervical sympathetic ganglion, a middle cervical sympathetic ganglion, or a lower cervical sympathetic ganglion. Examples of thoracic sympathetic ganglia can include a T1 sympathetic ganglia, a T2 sympathetic ganglia, a T3 sympathetic ganglia, a T4 sympathetic ganglia, a T6 sympathetic ganglia, or a T7 sympathetic ganglia.

Examples of spinal nervous tissue targets into which a therapy delivery device may be placed into electrical communication with can include, but are not limited to, a C1, C2, C3, C4, C5, C6, C7, or C8 spinal cord segment or spinal nervous tissue associated therewith, a T1, T2, T3, T4, T5, T6, T7, T8, T9, T10, T11, or T12 spinal cord segment or spinal nervous tissue associated therewith, a L1, L2, L3, L4, or L5 spinal cord segment or spinal nervous tissue associated therewith, or a S1, S2, S3, 54, or S5 spinal cord segment or spinal nervous tissue associated therewith.

After placing the therapy delivery device, the therapy delivery device can be activated to deliver a therapy signal (e.g., an electrical signal or magnetic field) to the autonomic nervous tissue target or spinal nervous tissue target. In some instances, delivery of a therapy signal to the autonomic nervous tissue target or spinal nervous tissue target can prevent a sign and/or symptom associated with autonomic instability or a medical condition associated therewith from either increasing or decreasing (as compared to a control or baseline). In other instances, delivery of a therapy signal to the autonomic nervous tissue target or spinal nervous tissue target can cause a sign and/or symptom associated with autonomic instability or a medical condition associated therewith to decrease as compared to a control or baseline). The therapy delivery device cat be activated at the onset of an episode (e.g., the onset of a sign and/or symptom) associated with autonomic instability or a medical condition associated therewith or, alternatively, the therapy delivery device can be activated continuously or intermittently to reduce or eliminate the frequency of such episode(s).

Delivery of the electrical signal to the autonomic nervous tissue target or spinal nervous tissue target can affect central motor output, nerve conduction, neurotransmitter release, synaptic transmission, and/or receptor activation at the target tissue(s). For example, the ANS may be electrically modulated to alter, shift, or change sympathetic and/or parasympathetic activity from a first state to a second state, where the second state is characterized by a decrease in sympathetic and/or parasympathetic activity relative to the first state. As discussed above, delivery of an electrical signal to the autonomic nervous tissue target or spinal nervous tissue target can, in some instances, substantially block activity of the autonomic nervous tissue target or spinal nervous tissue target. In other instances, delivery of an electrical signal to the autonomic nervous tissue target or spinal nervous tissue target can achieve a complete nerve conduction block of autonomic nervous tissue target or spinal nervous tissue target for a desired period of time. In other instances, delivery of an electrical signal to the autonomic nervous tissue target or spinal nervous tissue target can achieve a partial block of the autonomic nervous tissue target or spinal nervous tissue target for a period of time sufficient to decrease sympathetic and/or parasympathetic nerve activity. In further instances, delivery of an electrical signal to the autonomic nervous tissue target or spinal nervous tissue target can increase sympathetic tone (e.g., from a hyposypmathetic state) to a normal or baseline level. The degree to which sympathetic and/or parasympathetic activity is decreased or increased cat be titrated by one skilled in the art depending, for example, upon the nature and severity of autonomic instability or a medical condition associated therewith.

In another aspect, the present disclosure can include a method 20 (FIG. 4) for treating autonomic instability or a medical condition associated therewith in a subject. One step of the method 20 can include providing a therapy delivery device (Step 22). Alternatively, Step 22 can include providing a closed-loop therapy delivery system. Examples of suitable therapy delivery devices (and systems) are described above and further illustrated below. At Step 24, the therapy delivery device (or system) can be placed into electrical communication with an autonomic nervous tissue target or spinal nervous tissue target associated with autonomic instability or a medical condition associated therewith (e.g., a neurological or neurodegenerative disorder). In some instances, the therapy delivery device can be placed in direct electrical contact with the autonomic nervous tissue target or spinal nervous tissue target. "Direct electrical contact" can mean that the therapy delivery device (or system) is placed on or in the autonomic nervous tissue target or spinal nervous tissue target. In other instances, "direct electrical contact" can mean that the therapy delivery device (or system) is located adjacent or directly adjacent (but not in physical contact with) the autonomic nervous tissue target or spinal nervous tissue target such that delivery of a therapy signal (e.g., an electrical signal or a magnetic field) can modulate a function, activity, and/or characteristic of the autonomic nervous tissue target or spinal nervous tissue target.

Figure 4:
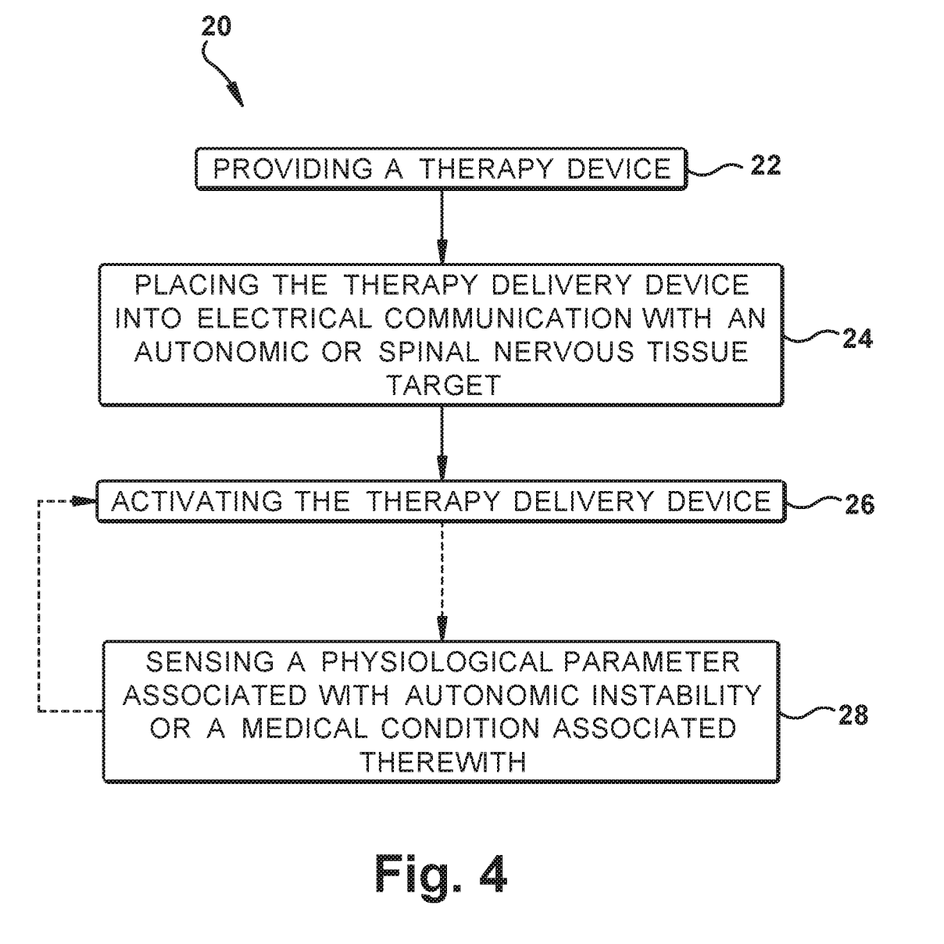
FIG. 4 is a process flow diagram illustrating a method for treating autonomic instability or a medical condition associated therewith according to another aspect of the present disclosure.

After placing the therapy delivery device (or system) into direct electrical communication with the autonomic nervous tissue target or spinal nervous tissue target, the therapy delivery device (or system) can be activated to deliver the therapy signal to the autonomic nervous issue target or spinal nervous tissue target (Step 26). The therapy signal can be delivered in an amount and for a time sufficient to effectively treat autonomic instability or a medical condition associated therewith. In one example, electrical energy can be delivered to the stellate ganglion by an electrode or electrode array that is placed directly on or in the stellate ganglion. In some instances, autonomic instability or a medical condition associated therewith may be caused by hyposympathetic activity. In such instances, it may be desirable to deliver continuous stimulation to the stellate ganglion to increase sympathetic activity in the subject so that the sympathetic tone of the subject (or the sympathetic tone of a particular organ or tissue) improves (e.g., to a normal level).

Figure 5:
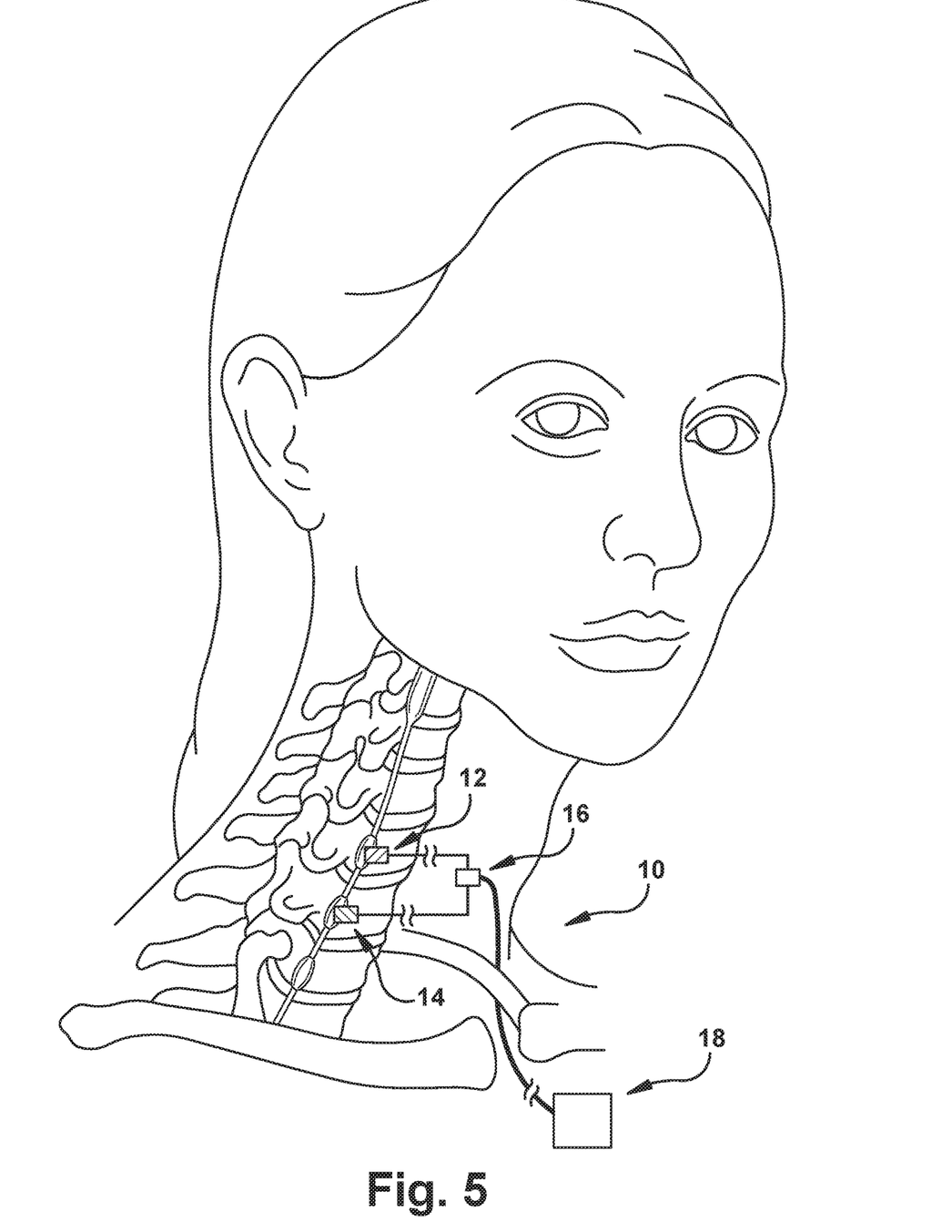
FIG. 5 is a schematic illustration showing the closed-loop therapy delivery system of FIG. 3 implanted in a subject.

One example of the method 20 is illustrated in FIG. 5. At Step 22, the method 20 can include providing a closed-loop therapy system 10 as described above. The closed-loop therapy system 10 can be configured for percutaneous implantation in the subject. As shown in FIG. 5, the system 10 can be implanted in the subject so that the delivery component 14 and the sensing component 12 are in direct electrical contact with the stellate ganglion and the middle cervical ganglion, respectively. Additionally, the system 110 can be implanted so that the controller 16 and the power source 18 are secured at the same or different subcutaneous locations.

Once the system 10 is implanted (Step 24), the sensing component 12 can detect electrical activity in the middle cervical ganglion, which may be indicative of intrinsic sympathetic tone in the subject. The detected level(s) of electrical activity can then be relayed to the controller 16, which determines if the detected level(s) is/are within a normal or abnormal range or level. Where the detected level(s) is/are within an abnormal range (e.g., at an elevated level as compared to a control a baseline), the controller 16 can cause the power source 18 to deliver an electrical signal to the delivery component 14. Stimulation parameters of the electrical signal as described herein can also be modulated. The electrical signal is then delivered to the stellate ganglion to modulate activity therein (Step 26). While the electrical signal(s) is/are being delivered to the stellate ganglion, the sensing component 12 can continue to detect the level of electrical activity within the middle cervical ganglion (Step 28). When the level of electrical activity in the middle cervical ganglion is equal, or about equal to, a normal or baseline level, the controller 16 can cease delivery of the electrical signal(s) to the delivery component 14. By continuously or intermittently monitoring the intrinsic sympathetic tone or activity of the subject, the closed-loop therapy delivery system 10 can automatically decrease or normalize abnormal sympathetic activity and thus effectively treat autonomic ins ability or a medical condition associated therewith.

Another aspect of the present disclosure can include transvascular or transluminal delivery of an electrical energy to an autonomic nervous tissue target or spinal nervous tissue target associated with autonomic instability or a medical condition associated therewith (e.g., a neurological or neurodegenerative disorder). Thus, in some instances, the method 20 can include providing a therapy delivery device (or system) configured for transvascular or transluminal insertion and placement within the subject. For instance, a therapy delivery device configured for intravascular or intraluminal placement in a subject can include an expandable electrode as disclosed in the '331 application. The therapy delivery device can be inserted into a vessel or lumen of the subject. Non-limiting examples of vessel and lumens into which the therapy delivery device can be inserted include arteries, veins, an esophagus, a trachea, a vagina, a rectum, or any other bodily orifice. The therapy delivery device can be surgically inserted into the vessel or lumen via a percutaneous, transvascular, laparoscopic, or open surgical procedure.

After inserting the therapy delivery device into the vessel or lumen, the therapy delivery device can be advanced (if needed) to an intraluminal target site so that the therapy delivery device is in electrical communication with the autonomic nervous tissue target or spinal nervous tissue target. In some instances, advancement of the therapy delivery device can be done under image guidance (e.g., fluoroscopy, CT, MRI, etc.). Intraluminal target sites can include intravascular or intraluminal dons at which the therapy delivery device can be positioned. For example, an intraluminal target site can include a portion of a vessel wall that is innervated by (or in electrical communication with) the autonomic nervous tissue target or spinal nervous tissue target. Examples of intraluminal target sites can include, without limitation, vascular or luminal sites innervated by and/or in electrical communication with any nervous tissue(s), of the SNS or PNS, such as ne ns, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion, afferents thereof, efferents thereof, a sympathetic chain ganglion, a thoracic sympathetic chain ganglion, an upper cervical chain ganglion, a lower cervical ganglion, an inferior cervical ganglion, and a stellate ganglion.

After placing the therapy delivery device, a therapy signal (e.g., an electrical signal or a magnetic field) can be delivered to the autonomic nervous tissue target or spinal nervous tissue target. The therapy signal can be delivered in an amount and for a time sufficient to effectively treat autonomic instability or a medical condition associated therewith.

In another aspect, the method 20 can include providing a therapy delivery device r system) configured for placement on the skin of the mammal. Examples of therapy delivery devices configured for transcutaneous delivery of one or more therapy signals are disclosed above and described in more detail below. In some instances, a therapy delivery device (or system) can be positioned about the subject, without penetrating the skin of the subject, so that the therapy delivery device is in electrical communication with an autonomic nervous tissue target or spinal nervous tissue target associated with autonomic instability or a medical condition associated therewith. Non-limiting examples of an autonomic nervous tissue target or spinal nervous tissue target into which the therapy delivery device can be placed into electrical communication are described above. After placing the therapy delivery device (or system), a therapy signal can be delivered to the autonomic nervous tissue target or spinal nervous tissue target. The therapy signal can be delivered in an amount and for a time sufficient to effectively treat autonomic instability or a medical condition associated therewith.

Figure 6:
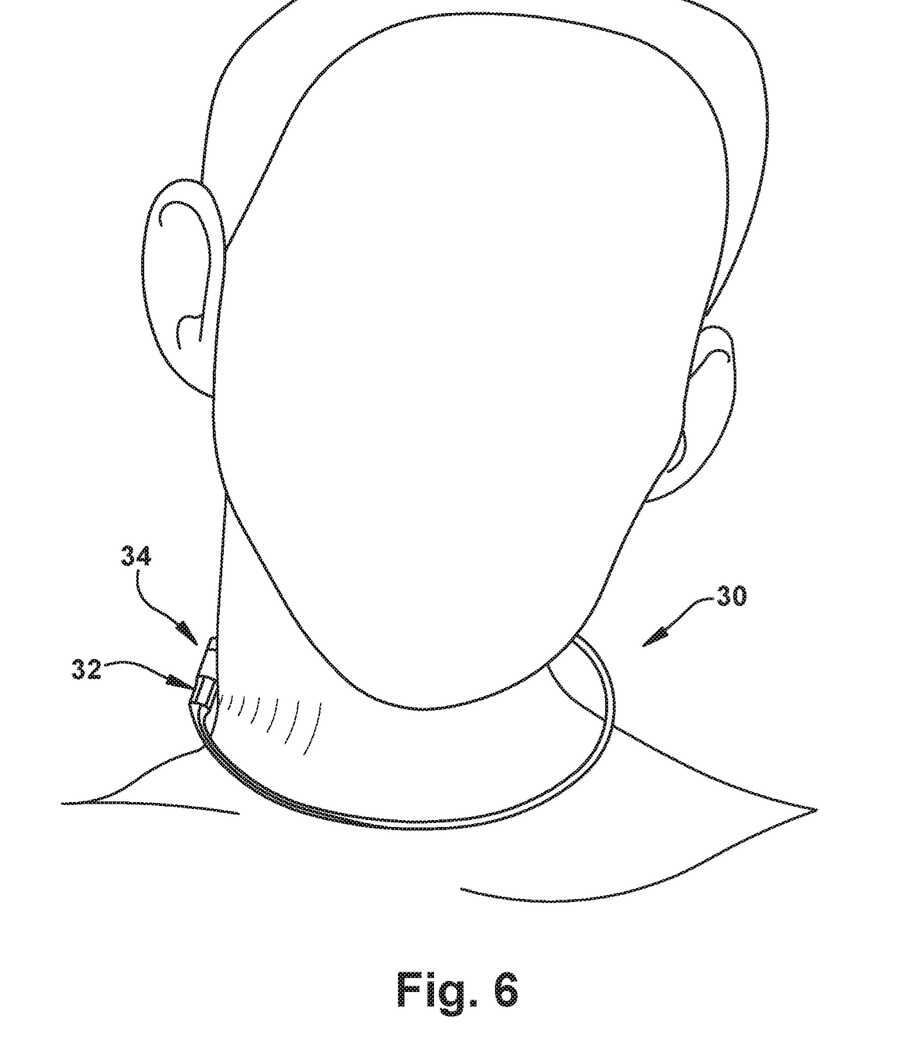
FIG. 6 is a schematic illustration showing a transcutaneous neuromodulatory device constructed in accordance with another aspect of the present disclosure.

In one example, transcutaneous neuromodulation device can comprise a wearable accessory item, such as a necklace or collar 30 (FIG. 6). As shown in FIG. 6, a necklace or collar 30 can be configured to include at least one electrode 32 for delivering a therapy signal to a particular region of a subject's neck (e.g., an anterior or posterior region thereof) depending upon the desired neuromodulatory effect, The necklace or collar 30 can additionally include an integral power source 34 (e.g., a rechargeable battery). It will be appreciated that the electrode(s) 32 can alternatively be powered by a wireless power source (not shown). The necklace or collar 30 can be configured to obtain a preselected position about a subject's neck by, for example, using a positioning guide (not shown), weighting the necklace or collar, etc. Alternatively, the subject can manually adjust the necklace or collar 30 as needed to optimize delivery of the therapy signal from the electrode(s) 32 to an autonomic nervous tissue target or spinal nervous tissue target.

Figure 7A:
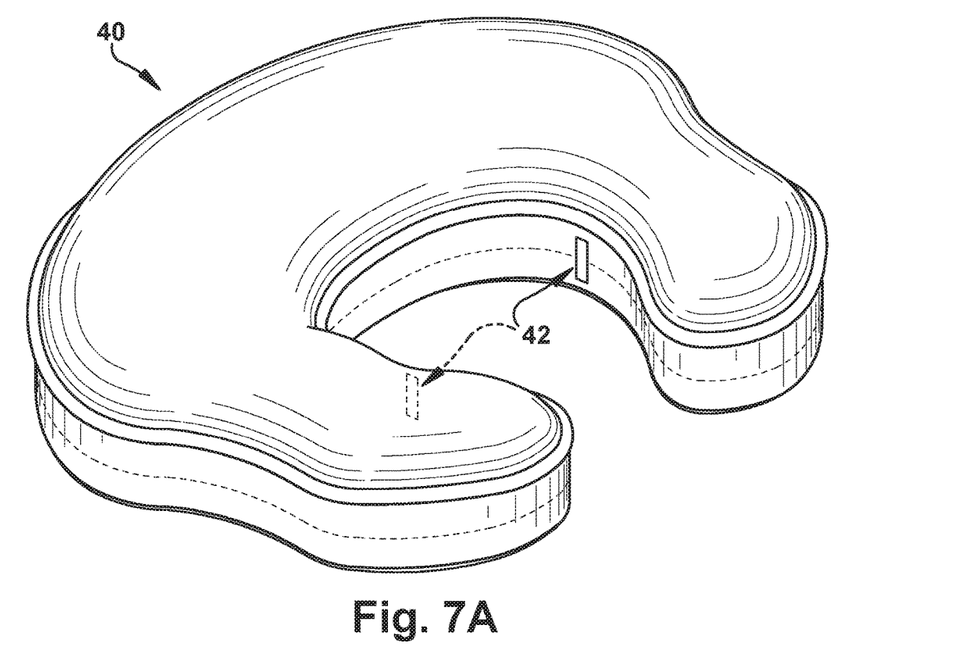
FIGS. 7A-B are schematic illustrations showing alternative transcutaneous neuromodulatory devices constructed in accordance with other aspects of the present disclosure.
Figure 7B:
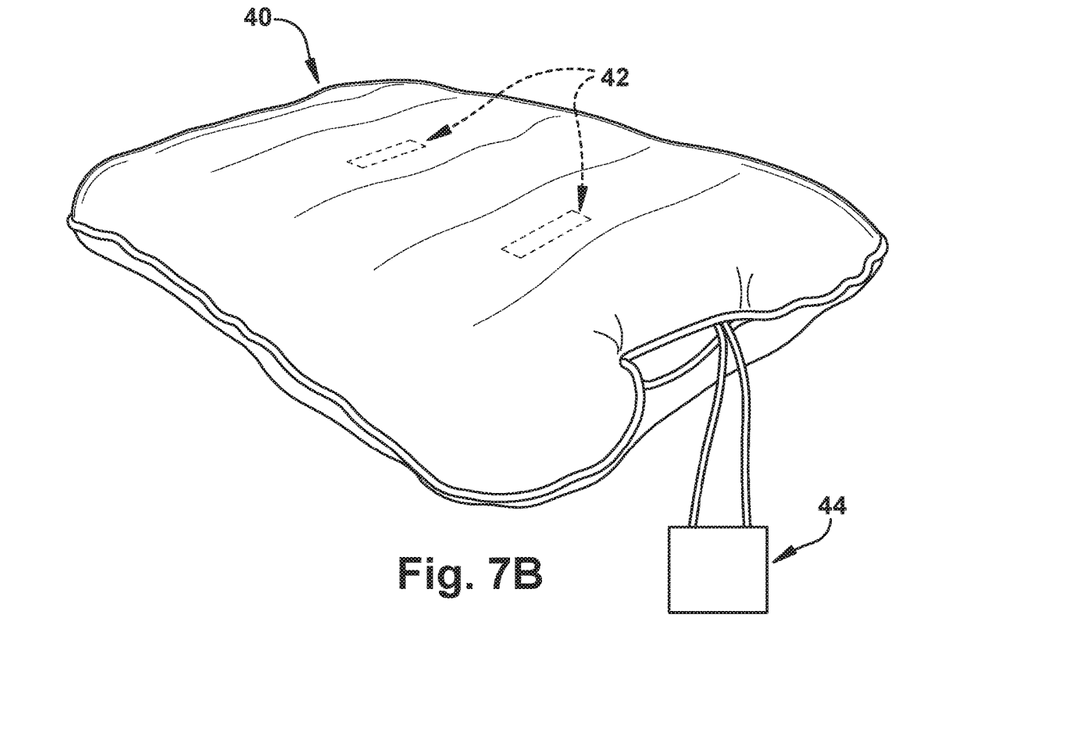

In another example, a transcutaneous neuromodulation device can comprise a pillow 40 (FIGS. 7A-B). In some instances, the pillow 40 (FIG. 7A) can be configured as a collar for use in a reclined or upright position, such as on an airplane, in a car, on a couch, etc. The pillow 40 can include at least one electrode 42 configured to deliver a therapy signal to an autonomic nervous tissue target or spinal nervous tissue target (e.g., in a subject's head or neck). As shown in FIG. 7A, the pillow 40 includes two oppositely disposed electrodes 42. The pillow 40 can also include a power source (not shown), which may be integrally connected with the pillow or located remotely (i.e., wirelessly) therefrom. In other instances, the pillow 40 (FIG. 7B) can comprise a traditional or conventional pillow for use when a subject is sleeping or lying in bed. As shown in FIG. 7B, the pillow 40 can include two oppositely disposed electrodes 42 configured to deliver a therapy signal to a target nerve when the subject neck or head is straddled between the electrodes. The pillow 40 can further include a power source 44 that is in direct electrical communication with the electrodes 42; however, it will be appreciated that the power source can be located remotely (i.e., wirelessly) from the pillow.

It will be appreciated that the transcutaneous neuromodulation devices illustrated in FIGS. 6 and 7A-B are illustrative only and, moreover, that such devices can include any wearable item, accessory, article of clothing, or any object, device, or apparatus that a subject can use and, during use, comes into close or direct contact with a portion of the subject's body (e.g., the subject's neck). Examples of such transcutaneous neuromodulation devices can include vests, sleeves, shirts, socks, shoes, underwear, belts, scarves, wrist bands, gloves, ear pieces, band-aids, turtle neck, pendants, buttons, earrings, stickers, patches, bio-films, skin tattoos (e.g., using neuro-paint), chairs, computers, beds, head rests (e.g., of a chair or car seat), cell phones, and the like.

Figure 8:
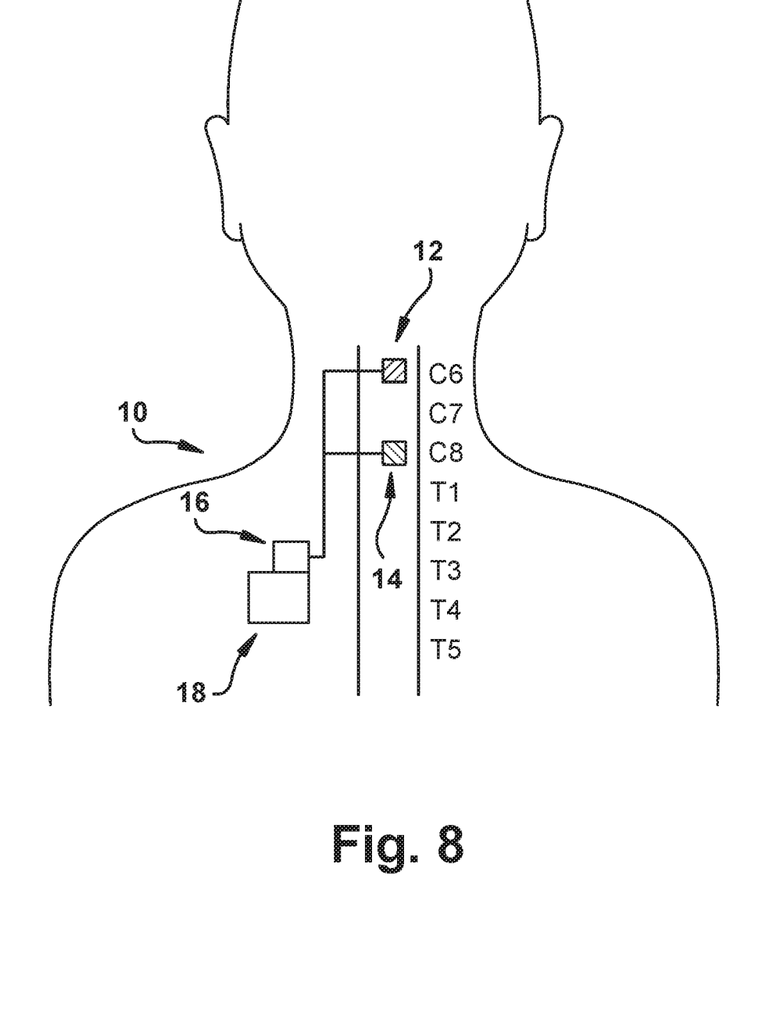
FIG. 8 is a schematic illustration showing the closed-loop therapy delivery system in FIG. 3 implanted in a human subject.

Another example of the method 20 is illustrated in FIG. 8. At Step 22, the method 20 can include providing a closed-loop therapy system 10 as described above. The closed-loop therapy system 10 can be configured for percutaneous (e.g., subcutaneous) implantation in the subject. As shown in FIG. 8, the system 10 can be implanted in the subject so that the delivery component 14 and the sensing component 12 are in direct electrical contact with a spinal cord segment at the level of C8 and a spinal cord segment at the level of C6, respectively. Additionally, the system 10 can be implanted so that the controller 16 and the power source 18 are secured at the same or different subcutaneous locations.

Once the system 10 is implanted (Step 24), the sensing component 12 can detect electrical activity in the C6 spinal cord segment, which may be indicative of intrinsic sympathetic tone in the subject. The detected level(s) of electrical activity can then be relayed to the controller 16, which determines if the detected level(s) is/are within a normal or abnormal range or level. Where the detected level(s) is/are within an abnormal range (e.g., at an elevated level as compared to a control or baseline), the controller 16 can cause the power source 18 to deliver an electrical signal to the delivery component 14. The electrical signal is then delivered to the spinal cord segment at the level of C8 to substantially block activity therein (Step 26). While the electrical signal(s) is/are being delivered to the spinal cord segment at the level of C8, the sensing component 12 can continue to detect the level of electrical activity within the spinal cord segment at the level of C6 (Step 28). When the level of electrical activity in the spinal cord segment at the level of C6 is equal, or about equal to, a normal or baseline level, the controller 16 can cease delivery of the electrical signal(s) to the delivery component 14. By continuously or intermittently monitoring the intrinsic sympathetic tone or activity of the subject, the closed-loop therapy delivery system 10 can automatically decrease or normalize hypersympathetic activity and thus effectively treat autonomic instability or a medical condition associated therewith.

From the above description of the present disclosure, those skilled in the art will perceive improvements, changes and modifications. Such improvements, changes, and modifications are within the skill of those in the art and are intended to he covered by the appended claims. All patents, patent applications, and publication cited herein are incorporated by reference in their entirety.

The following is claimed:

1. A closed-loop therapy delivery system for treating autonomic instability or a medical condition associated therewith in a subject, the therapy delivery system comprising:
   a sensing component configured to detect at least one physiological parameter associated with autonomic instability or the medical condition associated therewith;
   a delivery component configured for implantation on or about an autonomic nervous tissue target or a spinal nervous tissue target; and
   a controller configured to automatically coordinate operation of the sensing and delivery components;
   wherein the controller is programmed to deliver, to the delivery component, an electrical signal that substantially increases sympathetic activity at the autonomic nervous tissue target or a spinal nervous tissue target to effectively treat the autonomic instability or the medical condition associated therewith.

2. The system of claim 1, wherein the controller is programmed to deliver an electrical signal that substantially blocks activity at the autonomic nervous tissue target or a spinal nervous tissue target.

3. The system of claim 2, wherein the controller is programmed to deliver an electrical signal having a frequency of about 10,000 Hz to about 25,000 Hz.

4. The system of claim 1, wherein the at least one physiological parameter includes a chemical moiety or an electrical activity.

5. The system of claim 1, wherein the autonomic nervous tissue target is a ganglion of the sympathetic nervous system (SNS).

6. The system of claim 5, wherein the ganglion of the SNS is a cervical ganglion, a cervicothoracic ganglion, or a thoracic ganglion.

7. The system of claim 6, wherein the cervical ganglion is an upper, middle, or lower cervical ganglion.

8. The system of claim 1, wherein the spinal nervous tissue target is one of a cervical spinal cord segment, a thoracic spinal cord segment, a lumbar spinal cord segment, a sacral spinal cord segment, or spinal nervous tissue associated therewith.

9. A method for treating autonomic instability or a medical condition associated therewith in a subject, the method comprising the steps of:
   placing a therapy delivery device into electrical communication with a ganglion of the sympathetic nervous system or a spinal nervous tissue target associated with autonomic instability or the medical condition associated therewith; and
   activating the therapy delivery device to deliver an electrical signal to the ganglion of the sympathetic nervous system or the spinal nervous tissue target that substantially increases sympathetic activity in the ganglion of the sympathetic nervous system or the spinal nervous tissue target to effectively treat autonomic instability or the medical condition associated therewith in the subject.

10. The method of claim 9, further comprising the steps of:
    sensing at least one physiological parameter associated with autonomic instability or the medical condition associated therewith;
    generating a sensor signal based on the at least one physiological parameter; and
    activating the therapy delivery device to adjust application of the electrical signal to the ganglion of the sympathetic nervous system or the spinal nervous tissue target in response to the sensor signal to treat autonomic instability or the medical condition associated therewith.

11. The method of claim 10, wherein the at least one physiological parameter includes a chemical moiety or an electrical activity.

12. The method of claim 9, wherein the electrical signal has a frequency of about 10,000 Hz to about 25,000 Hz.

13. The method of claim 9, wherein the ganglion of the sympathetic nervous system is a cervical ganglion, a cervicothoracic ganglion, or a thoracic ganglion.

14. The method of claim 13, wherein the cervical ganglion is an upper, middle, or lower cervical ganglion.

15. The method of claim 9, wherein the spinal nervous tissue target is one of a cervical spinal cord segment, a thoracic spinal cord segment, a lumbar spinal cord segment, a sacral spinal cord segment, or spinal nervous tissue associated therewith.

16. The method of claim 9, wherein the medical condition associated with autonomic instability is a neurological condition.

* * * * *